United States Patent [19]
Reckelhoff et al.

[11] Patent Number: 5,304,190
[45] Date of Patent: Apr. 19, 1994

[54] ENDOSCOPIC CUTTING APPARATUS

[75] Inventors: Jerome E. Reckelhoff, Blue Ash; Mark Davison, Mason; William D. Kelly, Mason; Rudolph H. Nobis, Mason, all of Ohio

[73] Assignee: Ethicon, Inc., Cincinnati, Ohio

[21] Appl. No.: 881,003

[22] Filed: May 8, 1992

[51] Int. Cl.$^5$ .............................................. A61B 17/00
[52] U.S. Cl. ...................................... 606/170; 30/134; 30/241
[58] Field of Search ........................ 606/167, 170, 110; 30/278, 124, 241, 242, 243

[56] References Cited

U.S. PATENT DOCUMENTS

| | | | |
|---|---|---|---|
| 385,353 | 7/1888 | Hilton | 30/241 |
| 719,799 | 2/1903 | Hill | 30/241 |
| 2,316,297 | 4/1943 | Southerland et al. | |
| 2,541,063 | 2/1951 | Hubbard | |
| 3,484,940 | 12/1969 | Zell, Jr. | |
| 3,889,683 | 6/1975 | Kapitanov et al. | |
| 4,349,028 | 9/1982 | Green | |
| 4,569,346 | 2/1986 | Poirier | |
| 4,616,650 | 10/1986 | Green et al. | |
| 4,674,501 | 6/1987 | Greenberg | |
| 4,784,137 | 11/1988 | Kulik et al. | |
| 5,002,557 | 3/1991 | Hasson | 606/191 |
| 5,040,715 | 8/1991 | Green et al. | |
| 5,084,057 | 1/1992 | Green et al. | |
| 5,100,420 | 3/1992 | Green et al. | |
| 5,104,394 | 4/1992 | Knopfler | |
| 5,147,373 | 9/1992 | Ferzli | |
| 5,171,247 | 12/1992 | Hughett et al. | |
| 5,171,249 | 12/1992 | Stefanchik et al. | |
| 5,176,695 | 1/1993 | Dulebohn | |

OTHER PUBLICATIONS

Brochure by MTI Corporation, for precision arthroscopic instruments and multi-purpose knives.

Advertisement by DaVinci Medical for a hook cutter, appearing in Surgical Laparoscopy and Endoscopy, vol. 1, No. 3 (1991), Raven Press.

*Primary Examiner*—Stephen C. Pellegrino
*Assistant Examiner*—William Lewis

[57] ABSTRACT

An endoscopic cutting apparatus for use in endoscopic surgical procedures. The apparatus has a frame having a proximal end and a distal end. A handle is attached to the proximal end of the frame. Hook means are mounted to the distal end of the frame for engaging tissue or blood vessels. The hook means has a track means. Cutting blade means are mounted to said frame and are movable within said track means to cut tissue or blood vessels engaged within said hook means. Actuating means are mounted to the frame to actuate the cutting means in order to cut tissue or blood vessels engages within said hook means. Optional rotation means are mounted to the frame to allow the hook means and cutting means to rotate with respect to the frame. Optional extension means extend and retract the hook means into and out of the distal end of the frame.

6 Claims, 7 Drawing Sheets

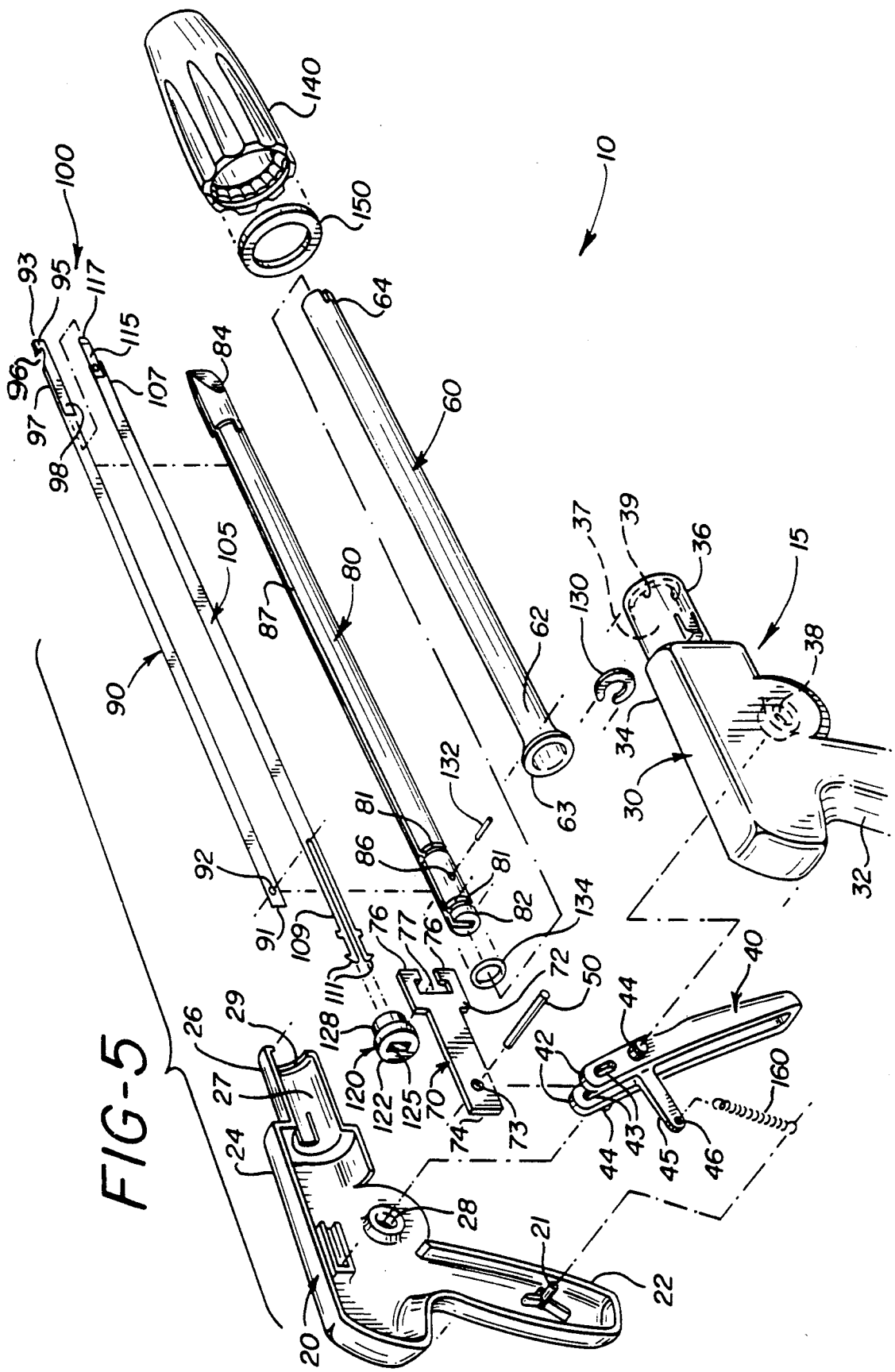

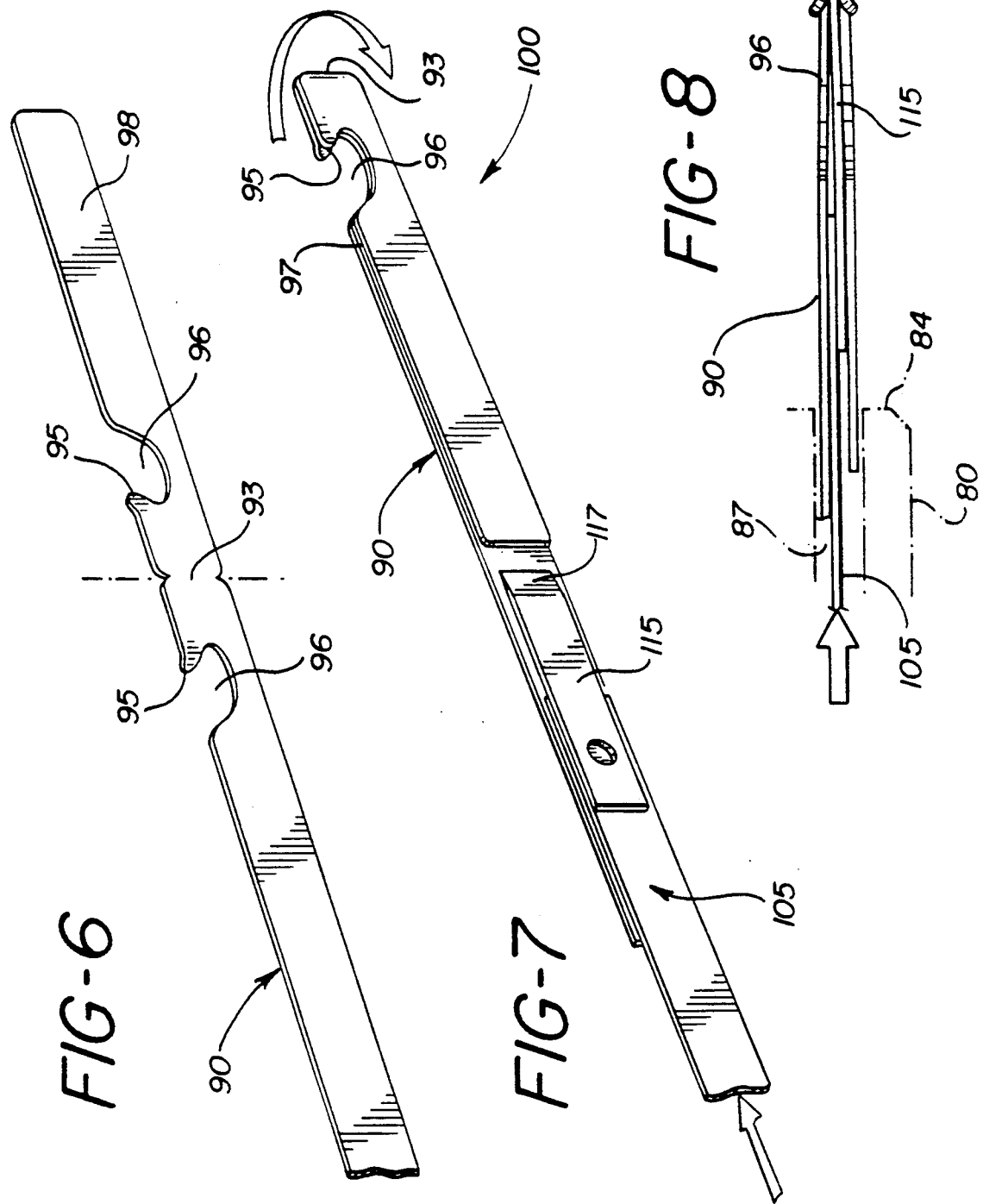

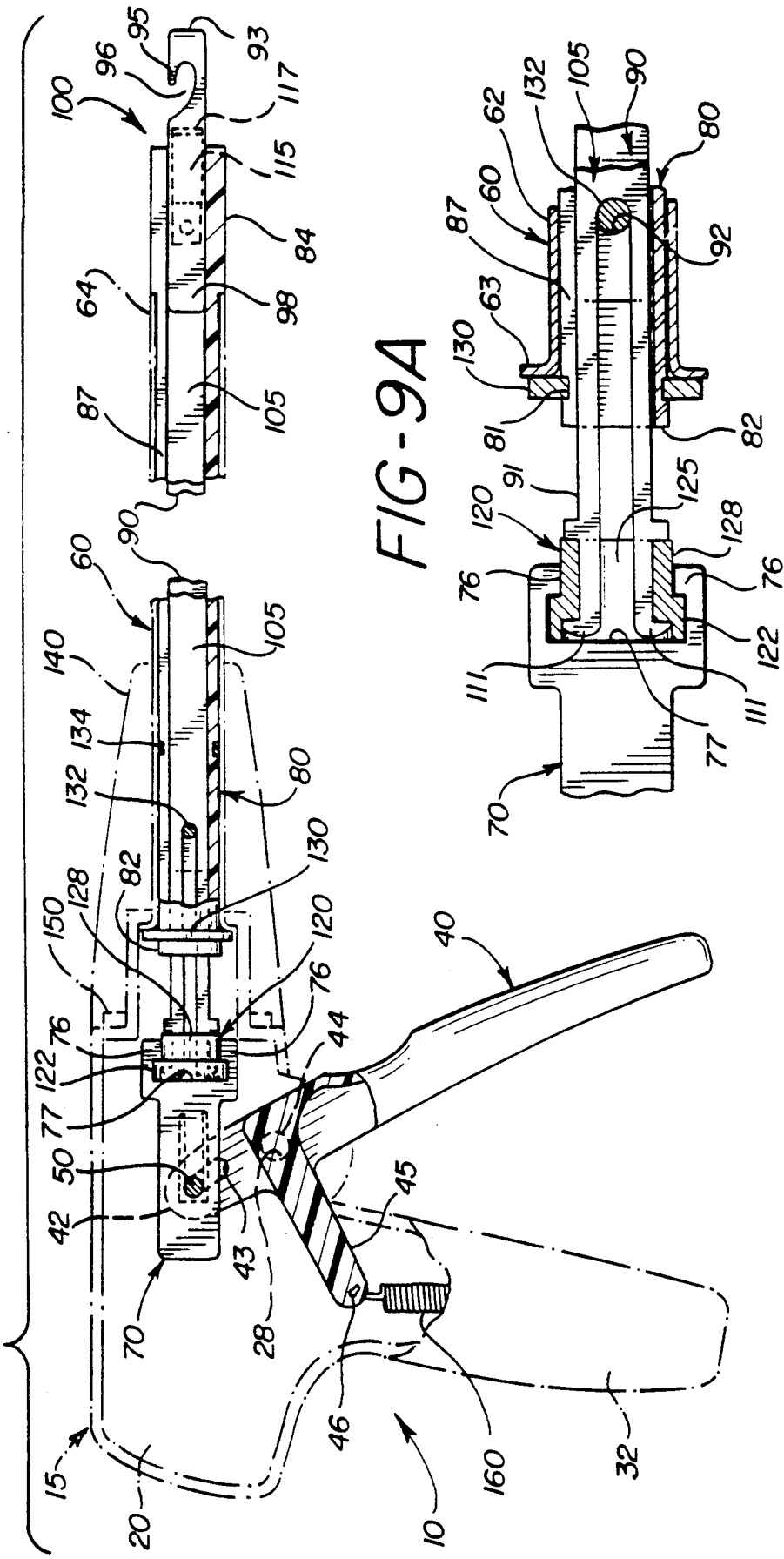

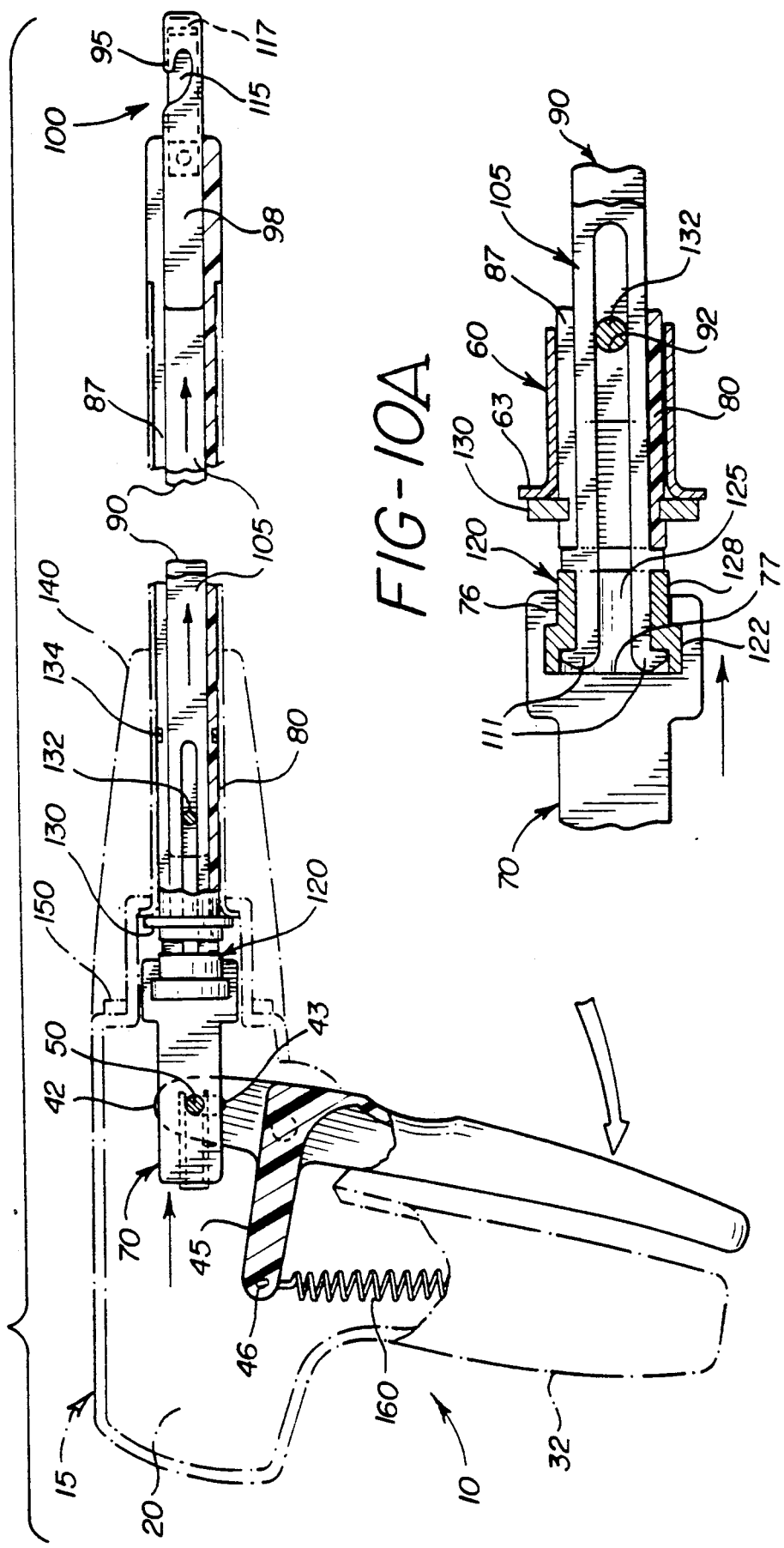

ENDOSCOPIC CUTTING APPARATUS

TECHNICAL FIELD

The field of art to which this invention relates is surgical instruments, in particular endoscopic surgical instruments.

BACKGROUND OF THE INVENTION

Endoscopic surgical techniques and procedures have become widely accepted both among the medical surgical community and the patient population. There are numerous benefits associated with the use of endoscopic surgical techniques rather than conventional open surgical techniques. These benefits include reduced avenues for infection, shortened post-operative recuperation period, decreased hospital stay and decreased scarring. It is not unusual for the post operative period to be shortened from weeks with conventional open surgery to several days with endoscopic surgical procedures, and outpatient endoscopic surgery is becoming more and more typical. The term endoscopic as used herein is defined to include endoscopic, laparoscopic, arthroscopic, and thorascopic.

In a typical endoscopic surgical procedure, the abdominal cavity of a mammal is typically insufflated with a sterile gas, such as carbon dioxide, in order to provide increased maneuvering room within the body cavity for endoscopic instruments. This procedure is typically referred to as inducement of pneumoperitoneum. Then, conventional trocars are inserted into the patients body cavity through the surrounding skin, tissue and musculature of the body cavity wall. A conventional trocar typically consists of a trocar cannula which houses an elongated trocar obturator. Trocar obturators typically have a piercing point, although other types of obturators are also available having blunt tips. Once the trocar has been positioned within the body cavity, proximal to the target surgical site, the trocar obturator is typically removed leaving the trocar cannula in place as a pathway to and from the target surgical site. The surgeon will place various types of endoscopic surgical instruments thorough the trocar cannulas in order to access the target surgical site where the surgical procedure will be performed. Examples of endoscopic instruments which have been developed for use with endoscopic surgical techniques include ligating clip appliers, electrosurgical instruments, endoscopes, tissue graspers, needle graspers, cannulas, tissue manipulators, endosurgical scissors, and the like.

Although endosurgical procedures and techniques offer many advantages, there are some deficiencies associated with these procedures and techniques. In particular, when the surgeon is operating using endoscopic surgical procedures, he is typically using an endoscope which is positioned within the body cavity through a trocar. The endoscope is typically connected to a video camera and the output from the video camera is displayed on a video monitor. The surgeon typically views the display on the video monitor as he manipulates instruments within the body cavity to access the target surgical site and perform the actual surgical procedures. The video display provides the surgeon with only two- dimensional input and there is a consequent loss of depth perception. This lack of depth perception may result in the surgeon over-shooting or under-shooting the target surgical site as he attempts to position various endoscopic instruments within the body cavity.

As can be appreciated, the internal organs of a mammal are very tightly packed within the body cavities. Therefore, the surgeon must exercise extreme care when maneuvering instruments through a body cavity to a target surgical site. This can be particularly difficult since, as was mentioned previously, the surgeon is working in a three dimensional space while viewing a two dimensional output. The degree of care which must be exercised by the surgeon is increased further when the surgeon is attempting to maneuver cutting instruments to the target surgical site. The cutting instruments which have been developed for use in endosurgical procedures consist of conventional endosurgical scissors and the like. The surgeon must be careful when maneuvering endoscopic cutting instruments, for example, endosurgical scissors, through a body cavity so that no internal organs or blood vessels are accidentally nicked or cut. In addition, it has been observed that endoscopic surgical scissors do not cut with the same efficiency as a conventional scalpel.

What is needed in this art is an endoscopic surgical cutting apparatus which will not accidentally nick or cut internal organs or blood vessels but which has improved cutting properties.

SUMMARY OF THE INVENTION

It is an object of the present invention to provide an endoscopic cutting apparatus which can be maneuvered through a body cavity without the cutting blade being exposed.

It is a further object of the present invention to provide an endoscopic cutting apparatus which has a means for engaging tissue or a blood vessel prior to and during cutting.

It is another object of the present invention to provide an endoscopic cutting apparatus which has improved tissue and blood vessel cutting characteristics.

Accordingly, an endoscopic cutting device is disclosed. The cutting device comprises a tubular frame having a proximal end and a distal end. A handle is mounted to the proximal end of the tubular frame. Hook means are mounted to the distal end of the tubular frame for engaging tissue or blood vessels prior to and during cutting. The hook means has track means contained therein for receiving a cutting blade means. The cutting blade means is mounted to the frame and is moveable within said track means to cut tissue or blood vessels engaged within the hook means. Actuating means are mounted to the frame for moving the cutting blade means.

Yet another aspect of the present invention is a method of cutting tissue or blood vessels in an endoscopic procedure using the above-described endoscopic cutting apparatus.

Still yet another aspect of the present invention is the combination of a trocar cannula and the above-described endoscopic cutting apparatus.

Other features and advantages of the invention will become more apparent from the following description and accompanying drawings.

BRIEF DESCRIPTION OF THE DRAWINGS

FIG. 5 is an exploded perspective view of the cutting apparatus of FIG. 1.

FIG. 6 is a partial perspective view of the distal end of the J-hook member prior to folding to form the isolation hook.

FIG. 7 is a partial perspective view of the distal end of the J-hook member and the distal end of the blade carrier and blade.

FIG. 8 is a partial top plan view of the cutting assembly of the cutting apparatus.

FIG. 9. is a side view partially in cross-section of the endoscopic cutting apparatus in a first, at-rest position.

FIG. 9A. is an enlarged, partial detailed view of the rotatable connection between the plunger plate and the blade carrier of the cutting apparatus of FIG. 9 showing the distal end of the plunger plate and the proximal end of the blade carrier.

FIG. 10 is a detailed view of the cutting apparatus similar to FIG. 9 in a second, actuated position.

FIG. 10A is an enlarged, partial detailed view of the apparatus of FIG. 10 similar to FIG. 9A showing the distal end of the plunger plate and the proximal end of the blade carrier after the cutting blade is actuated.

BEST MODE FOR CARRYING OUT THE INVENTION

Figure 1:
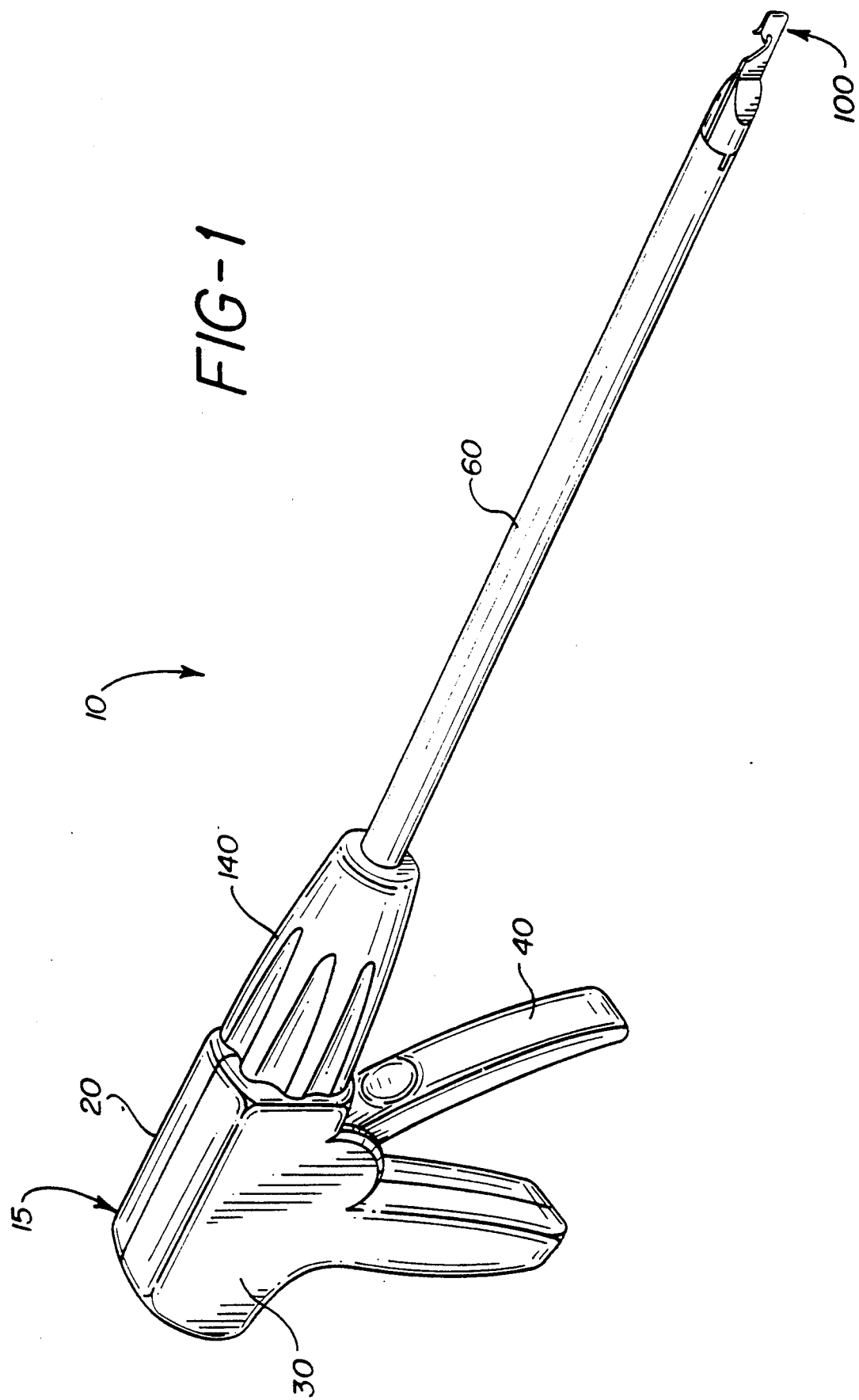
FIG. 1 is a perspective view of the endoscopic cutting apparatus of the present invention.

The endoscopic cutting apparatus 10 of the present invention is illustrated in FIG. 1, FIG. 2 FIG. 5, FIG. 9 and FIG. 10. The endoscopic cutting apparatus 10 is seen to have a hollow frame 15 consisting of left handle 20 and right handle 30. The left handle 20 is seen to have downwardly extending handle grip 22 and elongate section 24. The distal end 26 of left handle 20 is seen to have opening 27 for receiving the proximal end 62 of support tube 60. Extending from the inner wall of elongate section 24 is the journal bearing 28. Also extending from the inner wall of handle 22 is the spring mounting pin 21. The right handle 30 is similarly seen to have downwardly extending handle grip 32 and elongate section 34. The distal end 36 of the right handle 30 is seen to have opening 37 for receiving the proximal end 62 of support tube 60. Extending from the inner wall of elongate section 34 of right handle 30 is journal bearing 38.

Referring to FIGS. 5, 9, and 10, the trigger 40 is seen to be an elongate member. The yoke members 42 extend upwardly from either side of the top of the trigger 40. Yoke members 42 contain slots 43. Cylindrical shaft members 44 extend from either side of the trigger 40 below the yoke members 42. Trigger 40 is pivotally mounted in journal bearings 28 and 38 by inserting cylindrical shaft members 44 therein. Trigger arm 45 containing hole 46 is seen to extend proximally from the trigger 40.

The support tube 60 is an elongate tubular member having proximal end 62 and distal end 64. The flange member 63 is seen to extend radially outward from proximal end 62 of support tube 60.

The plunger plate 70 is seen to be an elongate plate member having proximal end 72 and distal end 74. Extending from distal end 74 are upper and lower hook members 76 which form C-shaped slot 77. Located in the proximal end 72 of the plunger plate 70 is the drive hole 73. The plunger plate 70 is mounted to trigger 40 by placing the proximal end 72 of the plunger plate 70 between the yoke members 42 such that the drive hole 73 of the plunger plate 70 is in alignment with the slots 43 of the yoke members 42. Then the drive pin 50 is inserted through the slots 43 and the drive hole 73.

Referring now to FIGS. 5, 6, 7 and 8, the blade assembly 100 is seen to consist of the blade carrier 105 and the blade 115. The blade carrier 105 has distal end 107 and proximal end 109. Extending proximally from proximal end 109 are a pair of opposed coupling prongs 111. Mounted to the distal end 107 of blade carrier 105 is the blade 115. Blade 115 is seen to have distal cutting edge 117. The blade 115 is mounted to the distal end 107 of the carrier 105 using conventional mounting methods including riveting and welding.

The J-hook member 90 is an elongate plate-like member having proximal end 91 and distal end 93. Located in the distal end 93 of the J-hook member 90 is the isolation hook 95 containing vessel hook aperture 96 and blade track 97. As can be seen in FIGS. 6, 7 and 8, the isolation hook 95 is formed by folding a section 98 of the distal end of the J-hook member 90 over and onto itself and then cutting out the vessel hook aperture 96 using conventional methods including gas burning, laser cutting, and the like. The isolation hook 95 may also be formed by cutting out apertures prior to folding in two places on the distal end 93 of the J-hook member 90 so that when the section 98 of the distal end of J-hook member 90 is folded over to form the isolation hook 95, the apertures are in substantial alignment to form the vessel hook aperture 96. J-hook member 90 is seen to have proximal mounting hole 92.

Referring to FIGS. 5, 9, and 10, the shroud 80 is seen to be an elongate cylindrical member having distal end 84 and proximal end 82. The shroud 80 has elongate axial slot 87 for receiving J-hook member 90 and blade assembly 100. Located at the proximal end 82 of the shroud 80 are the grooves 81 and the mounting hole 86. The J-hook member 90 and blade assembly 100 are mounted within slot 87 of shroud 80. The J-hook member 90 is attached to the shroud 80 by the retaining pin 132 which is inserted through the hole 86 located in the proximal end 82 of shroud 80 and through the hole 92 located in the proximal end 91 of J-hook member 90. The blade assembly 100 is slideably mounted within the slot 87 of shroud 80. The distal end 107 of the blade carrier 105 and the blade 115 are slideably contained within the track 97 of isolation hook 95. The O-ring 134 is mounted into the groove 81 distal to the mounting hole 86. The shroud 80 containing blade assembly 100 and the J-hook member 90 is mounted within support tube 60. The shroud 80 containing the blade assembly 100 and the J-hook member 90 is secured to the support tube 60 by the retaining ring 130 which is snapped into the groove 81 proximal to the mounting hole 86.

The plunger coupling 120 is seen to be a bushing-like member having outwardly extending proximal flange section 122 and axial cylindrical section 128. Axial cavity 125, having a rectangular cross-section, extends through the flange 122 and the cylindrical section 128 ( see FIG. 9A). The flange section 122 of the plunger coupling 120 is rotatably engaged within the C-shaped slot 77 of the plunger plate 70. The proximal coupling prongs 111 of blade carrier 105 are engaged within the axial cavity 125 of the plunger coupling 120 thereby allowing rotation of the blade assembly 100 with respect to plunger plate 70.

As can be seen in FIG. 5, proximal end 62 of the support tube 60 is rotatably mounted within the distal ends 26 and 36 of the left handle 20 and the right handle 30, respectively, thereby allowing rotation of support tube 60 with respect to the frame 15. The frame 15 is formed by mounting the right handle 30 to the left handle 20 using conventional mounting methods such as ultrasonic welding, bonding, fastening and the like. The support tube 60 is prevented from displacing longitudinally by the shoulders 29 and 39 contained in the left handle 20 and right handle 30, respectively. The return spring 160 is seen to be connected on one end to the pin 21 in the left handle 20 and on the other end to the hole 46 contained in the trigger arm 45. The spring 160 provides a counterclockwise biasing force on the trigger 40. The knob ring 150 is mounted to the knob 140 in a conventional manner to form a knob assembly which is rotatably mounted to the distal end of frame 15 and keyed to the proximal end of support tube 60 to assist in rotating the support tube with respect to the frame 15.

Figure 4:
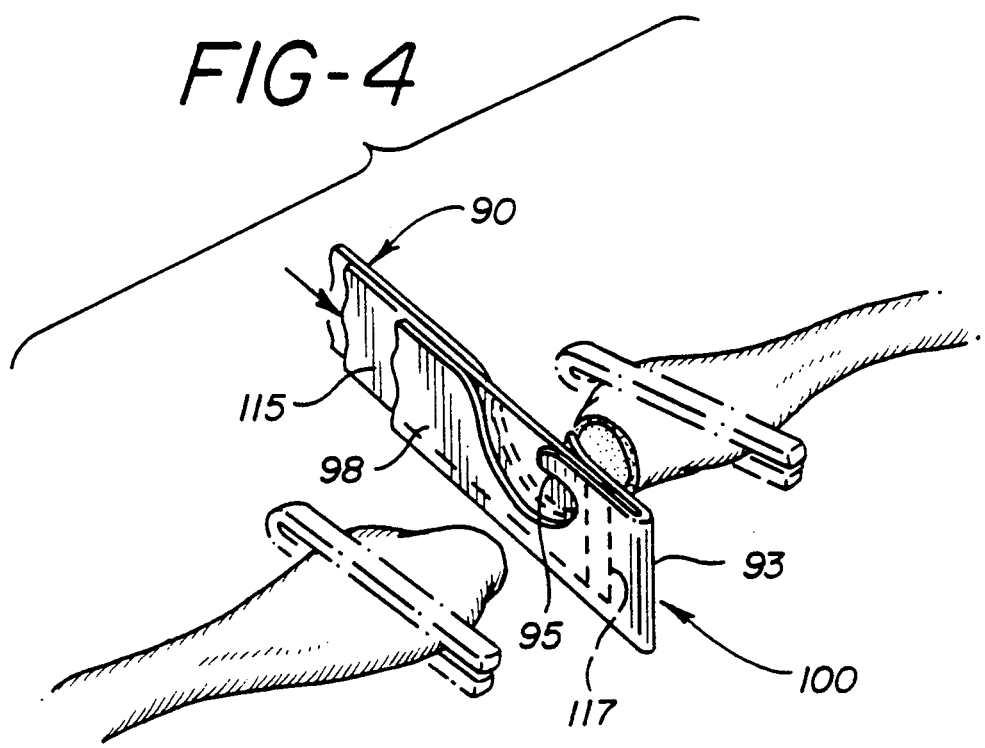
FIG. 4 is a partial perspective view of the distal end of the J-hook member after the blade has cut a blood vessel contained within the isolation hook.

The cutting apparatus 10 is actuated by squeezing the trigger 40 causing it to rotate in a clockwise manner about journal bearings 28 and 38 as shown in FIG. 10. As the trigger 40 is rotated, the yoke members 42 also rotate causing the drive pin 50 to displace longitudinally. Since the drive pin 50 is engaged by the plunger plate 70 at drive hole 73, the rotation of trigger 40 also causes plunger plate 70 to displace distally in a longitudinally axial manner. The plunger coupling 120, which is rotatably engaged in the C-shaped slot 77 of the plunger plate 70, also engages the proximal members 111 of the blade assembly 100. Displacement of the plunger plate 70 also causes the blade assembly 100 to be displaced within the slot 87 of the shroud 80 and the track 97 of the J-hook member 90. This causes the blade 115 to displace distally through the vessel hook aperture 96 contained in the isolation hook 95. This allows the blade 115 to sever tissue or blood vessels contained within the vessel hook aperture 96 (also shown in FIG. 4). The blade assembly 100, the plunger coupling 120, the plunger plate 70, the drive pin 50 and the trigger 40 are returned to an at-rest position (see FIG. 9) when the trigger is released because of the counterclockwise bias force of the return spring 160 acting on the trigger arm 45 of trigger 40.

Figure 2:
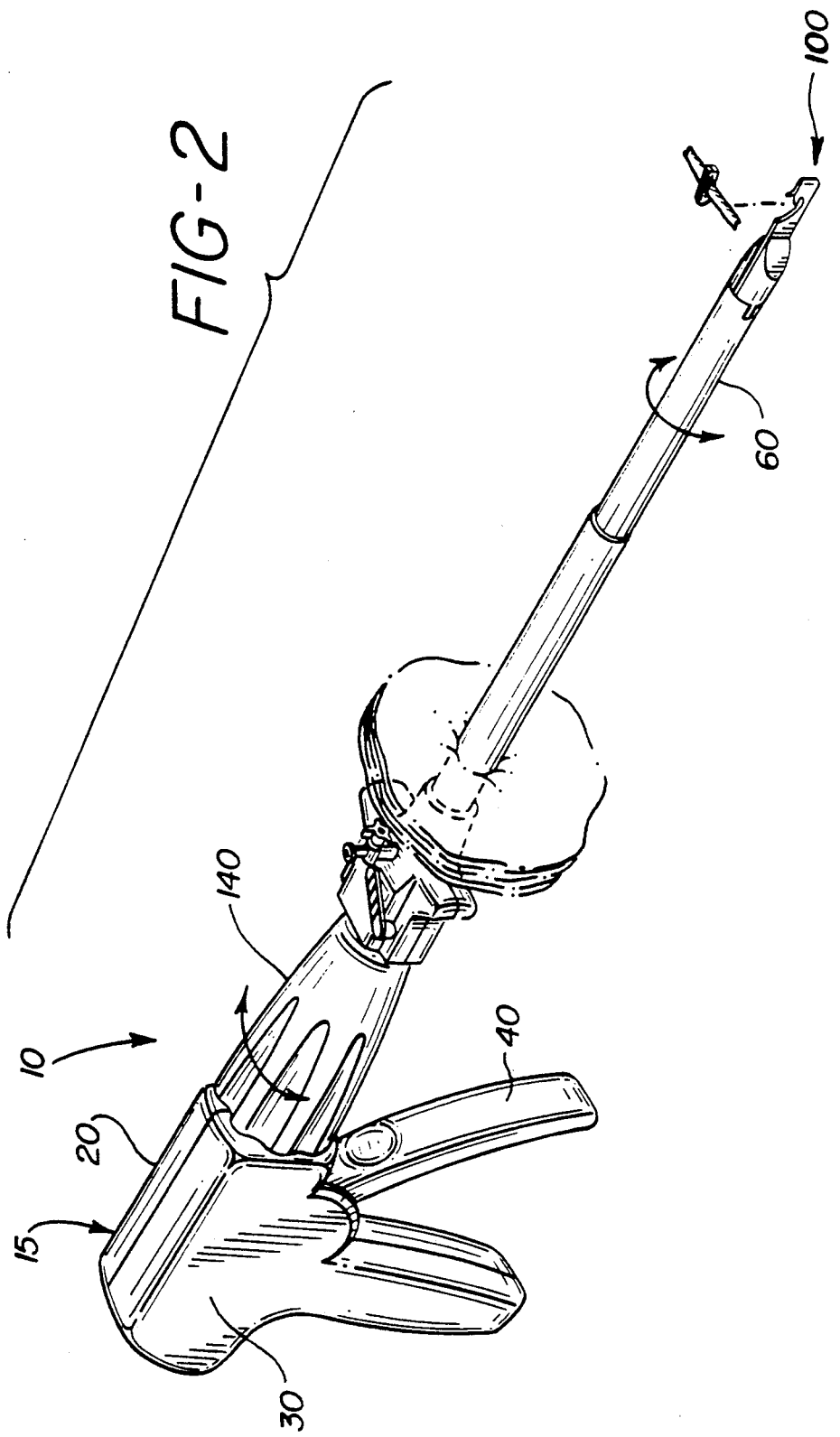
FIG. 2 is a perspective view of the cutting apparatus inserted through a trocar cannula into a body cavity.
Figure 3:
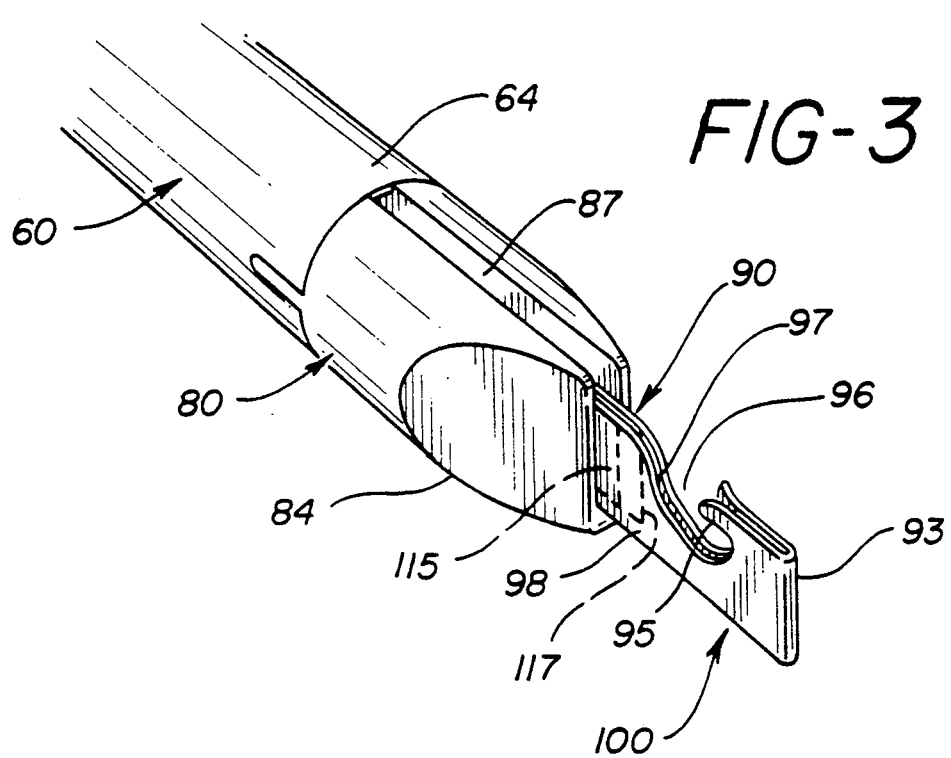
FIG. 3 is an enlarged fragmentary view of the distal end of the cutting apparatus showing the distal end of the J-hook member.

The support tube 60, shroud 80, J-hook member 90 and blade assembly 100 can rotate with respect to the left handle 20 and right handle 30 and the plunger plate 70. The flange 63 of the support tube 60 is rotatably mounted in the frame 15. And, plunger coupling 120 is rotatably engaged within the C-shaped slot 77 of the plunger plate 70 thereby allowing the blade assembly 100 to rotate with respect to the plunger plate 70. Rotating the knob 140 causes the support tube 60 and the assembly contained therein to rotate with respect to the frame 15 as seen in FIG. 2.

In another embodiment of the cutting apparatus of the present invention (not shown in the drawings) extension means are mounted to the frame 15 to extend and retract isolation hook 95. The extension means will typically consist of an extension plate slideably mounted, axially, in the frame 15 and rotatably connected at its distal end to the proximal end of J-hook member 90 which will also be slideably mounted. Typically, a button slideably mounted to the exterior of the frame 15 and connected to the extension plate will actuate the extension plate causing the J-hook member 90 to slide axially within the slot 87 of shroud 80. This in turn will cause the isolation hook 95 to slide into and out of the distal end of the apparatus 10. In this embodiment of apparatus 10, the isolation hook 95 is typically in a retracted position prior to insertion into a trocar cannula. The distal end of the apparatus 10 is maneuvered proximal to the target blood vessel or tissue at which time the isolation hook 95 is extended by actuating the extension mechanism and the apparatus 10 is then used in a manner as previously described.

The endoscopic cutting apparatus 10 of the present invention will be constructed from materials conventional in this art. The materials include plastics such as polycarbonate, nylon, polyetherimide and nitrile as well as the 300 and 400 series stainless steels and the like and equivalents thereof. The edge 117 of the blade 115 will be manufactured using conventional blade edge forming methods including grinding with conventional grinding apparatus and the like. The apparatus 10 is typically packaged in conventional packaging materials. The endoscopic cutting apparatus 10 is typically sterilized after packaging and prior to use using conventional sterilization techniques. It is particularly preferred to sterilize the apparatus 10 using cobalt-60 generated radiation, although other types of sterilization including autoclaving and ethylene oxide sterilization may be used.

The endoscopic cutting apparatus 10 may be used in conventional endoscopic techniques including cholecystectomy, appendectomy, anastomosis, hernia repair and the like. Endoscopic surgical techniques and procedures are widely known, e.g., endoscopic surgical techniques are disclosed in the following publications which are incorporated by reference: Textbook of Laparoscopy, Jaroslav Hulka, M.D., Grune & Stratton, Inc., New York (1985) and Laparoscopy for Surgeons, Barry A. Salky, M.D., Igaku-Shoin, New York(1990). When utilizing endosurgical techniques, initially a patient is typically anesthetized using a sufficient dose of anesthesia effective to induce an anesthetized state. Conventional anesthesiology techniques and procedures are utilized including, where needed, the use of an endotracheal tube and a ventilator. The next step after the application of anesthesia is the insufflation of the body cavity containing the target surgical site. This is done using conventional techniques and equipment. The gases which are typically used for insufflation include conventional sterile gases such as carbon dioxide and the like. After the body cavity has been insufflated sufficiently so that the surgeon has room to effectively manipulate and maneuver instrumentation within the body cavity, several conventional trocars are inserted in a conventional manner through the body cavity wall into the body cavity, for example, the abdominal cavity. Conventional trocars typically comprise a piercing obturator concentrically housed in a trocar cannula. After the trocars are inserted, the piercing obturators are then removed from the trocar cannulas leaving the trocar cannulas as pathways to the body cavity. Conventional endoscopic instrumentation is inserted through the cannulas including endoscopes, staplers, sutures, cannulas, electrosurgical instruments, ligating clip appliers, and the like. The instruments are maneuvered to the target surgical site where a surgical procedure is performed. The surgeon views the interior of the body cavity and the target surgical site by observing the output from the endoscope. Conventional endoscopes typically are connected to video cameras and the output displayed on a video monitor.

One of the crucial endoscopic techniques which must be mastered by the surgeon when utilizing endoscopic procedures is the ability to maneuver instruments in a three-dimensional body cavity while observing a two-dimensional visual output on the video display of the endoscope. This requires both skill and judgment based upon the experience of having performed previous operations. When using conventional endoscopic scissors, the surgeon must locate the vessel or tissue to be cut and engage the vessel or tissue between the blades of the scissors. The surgeon maneuvers the endoscopic scissors in position about the intended cut and then makes the cut in the tissue. As previously mentioned, the physician is maneuvering in a three-dimensional body cavity, however, he only has two-dimensional input from the video display of the endoscope. Therefore, the surgeon must use extreme care in maneuvering the scissors to the tissue or blood vessel where the cut is to be made. The surgeon must use judgment in deciding whether the tissue or blood vessel is properly contained within the jaws of the conventional scissors when cutting since the scissors do not provide for positive retention. There is also an element of hazard present requiring extra care as the surgeon attempts to maneuver the cutting instrument in the relatively cramped space in the body cavity. The hazards include accidental nicking or cutting of organs or blood vessels or tissue. In addition, endoscopic scissors tend not to cut well and become dull very rapidly.

Using the endoscopic cutting apparatus 10 of the present invention, these deficiencies are eliminated. The cutting mechanism 10 of the present invention is inserted through a trocar cannula into a body cavity and maneuvered by the surgeon to the target surgical site where a blood vessel or tissue is to be cut, as shown in FIG. 2. The endoscopic cutting apparatus 10 is a cutting instrument which can engage and cut tissue and which may also be used to maneuver tissue or blood vessels. The surgeon positions the blood vessel or tissue within the vessel hook aperture 96 of the J-hook member 90. The surgeon can see on the endoscope video monitor that the tissue or blood vessel is positively contained within the vessel hook aperture 96. The surgeon then actuates the blade assembly 100 by squeezing the trigger 40 which causes the blade assembly 100 and the blade 115 to travel distally such that blade 115 displaces distally through track 97 in isolation hook 95 thereby cutting the blood vessel or tissue engaged within the vessel hook aperture 96 in the isolation hook 95 of J-hook member 90.

It will be appreciated by those skilled in the art that the cutting apparatus 10 of the present invention can be used not only in endoscopic surgical procedures but also in conventional open procedures. It will also be appreciated that the apparatus 10 may, if one were willing to accept whatever disadvantages may be present, if any, be inserted through a small slit directly into a body cavity without a conventional trocar.

The following example is illustrative of the principles and practice of the present invention although not limited thereto.

EXAMPLE

A mammal is prepared for surgery using conventional surgical techniques. A sufficient dose of a conventional anesthesia is administered using conventional anesthesiology techniques effective to induce an anesthetized state. The abdominal cavity of the patient is then sufficiently insufflated using conventional insufflation equipment and techniques with carbon dioxide gas to produce an effective pneumoperitoneum. Three trocars are then inserted through the abdominal wall of the mammal into the abdominal cavity. The trocars are conventional trocars having elongated obturators with piercing tips concentrically housed in trocar cannulas. The trocar obturators are then removed leaving the trocar cannulas as pathways to the abdominal cavity. An endoscope is inserted through one of the trocar cannulas. The output from the endoscope is displayed on a video monitor. The surgeon observes the interior of the abdominal cavity on the video monitor and maneuvers instruments into position using the video monitor display. The endoscopic cutting apparatus 10 of the present invention is inserted through one of the trocar cannulas. The surgeon maneuvers the distal end of the apparatus 10 to a position proximate to a target blood vessel which is to be ligated. The surgeon then positions the blood vessel within the vessel hook aperture 96 in the isolation hook 95 of J-hook member 90. The blood vessel is positively engaged within the aperture 96 in isolation hook 95 and the surgeon is easily able to observe this positive engagement on the endoscope video monitor. The surgeon then manipulates the position of the blood vessel with the apparatus 10. Typically, prior to cutting, the blood vessel or tissue is ligated with a conventional ligating clip applier which is used to apply ligating clips to the blood vessel or tissue on either side of the intended cut. The surgeon then actuates the cutting apparatus 10 by squeezing the trigger 40 such that the cutting blade 115 advances distally through the blood vessel contained within the vessel hook aperture 96 in the isolation hook 95. As the surgeon releases the trigger 40, the blade 115 is automatically retracted from the vessel hook aperture 96 in isolation hook 95. The surgeon then withdraws the distal end of the apparatus 10 from the body cavity and out through the trocar cannula The surgeon then removes the trocar cannulas and closes up the wounds using conventional techniques including stapling, suturing, and/or taping.

The endoscopic cutting apparatus 10 of the present invention provides a means for cutting tissue or blood vessels. The possibility of inadvertently cutting or nicking blood vessels, tissue or organs is minimized. Tissue or blood vessels are easily positively engaged within the vessel hook aperture of the isolation hook 95. The surgeon is readily able to see on the endoscopic video display that tissue or blood vessels are positively retained and engaged within the vessel hook aperture 96 of isolation hook 95 prior to cutting. When using endoscopic scissors, the surgeon must use skill and judgment to determine when the tissue is within the open scissor blades. There is no positive tissue or blood vessel retention provided by conventional endoscopic scissors, the surgeon is not able to perceive from the endoscopic video display whether or not the tissue or blood vessel is absolutely positioned within the scissor jaws. In addition, the cutting blade 115 of the apparatus 10 cuts quickly and repeatedly without the blade edge 117 becoming dull. In contrast, it is known that endoscopic scissors become dull very quickly. Another advantage of the apparatus 10 of the present invention is that the isolation hook 95 can be easily manufactured in one preferred embodiment by folding the section 98 of the distal end 93 of the J-hook member 90 over and onto itself to form the track 97 and the isolation hook 95.

Although this invention has been shown and described with respect to detailed embodiments thereof, it will be understood by those skilled in the art that various changes in form and detail thereof may be made without departing from the spirit and scope of the claimed invention.

What is claimed is:

1. An endoscopic cutting apparatus comprising
    an elongate frame having a proximal end and a distal end;
    a handle attached to the proximal end of said frame;
    hook means for engaging tissue or blood vessels mounted to the distal end of said frame, said hook means having track means;
    cutting blade means mounted to said frame and movable, axially, within said track means;
    actuating means mounted to said frame for moving said blade means in said track means axially through said hook means for cutting tissue or blood vessels engaged by said hook means; and
    rotation means allowing the hook means to rotate with respect to the frame.

2. An endoscopic cutting apparatus comprising
    an elongate frame having a proximal end and a distal end;
    a handle attached to the proximal end of said frame;
    hook means for engaging tissue or blood vessels mounted to the distal end of said frame, said hook means having track means, said hook means comprising a plate member folded over onto itself to form a track, and, a hook-shaped opening therein;
    cutting blade means mounted to said frame and movable, axially, within said track means; and actuating means mounted to said frame for moving said blade means in said track means axially through said hook means for cutting tissue or blood vessels engaged by said hook means.

3. A method of cutting a blood vessel or tissue, comprising:
    inserting an endoscopic cutting apparatus into a body cavity of a mammal;
    engaging the blood vessel or tissue with the apparatus;
    using the cutter to cut the blood vessel or tissue wherein the apparatus comprises:
    an elongate frame having a proximal end and a distal end;
    a handle attached to the proximal end of said frame;
    hook means for engaging tissue or blood vessels mounted to the distal end of said frame, said hook means having track means;
    cutting blade means mounted to said frame and movable, axially, within said track means;
    actuating means mounted to said frame for moving said blade means in said track means axially through said hook means for cutting tissue or blood vessels engaged by said hook means; and
    said cutting apparatus further comprising rotation means allowing the hook means to rotate with respect to the frame.

4. A method of cutting a blood vessel or tissue, comprising:
    inserting an endoscopic cutting apparatus into a body cavity of a mammal;
    engaging the blood vessel or tissue with the apparatus;
    using the cutter to cut the blood vessel or tissue wherein the apparatus comprises:
    an elongate frame having a proximal end and a distal end;
    a handle attached to the proximal end of said frame;
    hook means for engaging tissue or blood vessels mounted to the distal end of said frame, said hook means having track means, said hook means comprising a plate member folded over onto itself to form a track, and, a hook-shaped opening therein;
    cutting blade means mounted to said frame and movable, axially, within said track means; and
    actuating means mounted to said frame for moving said blade means in said track means axially through said hook means for cutting tissue or blood vessels engaged by said hook means.

5. The combination of a trocar cannula and an endoscopic cutting apparatus wherein the cutting apparatus comprises:
    an elongate frame having a proximal end and a distal end;
    a handle attached to the proximal end of said frame;
    hook means for engaging tissue or blood vessels mounted to the distal end of said frame, said hook means having track means;
    cutting blade means mounted to said frame and movable, axially, within said track means;
    actuating means mounted to said frame for moving said blade means in said track means axially through said hook means for cutting tissue or blood vessels engaged by said hook means; and
    rotation means allowing the hook means to rotate with respect to the frame.

6. The combination of a trocar cannula and an endoscopic cutting apparatus wherein the cutting apparatus comprises:
    an elongate frame having a proximal end and a distal end;
    a handle attached to the proximal end of said frame;
    hook means for engaging tissue or blood vessels mounted to the distal end of said frame, said hook means having track means, said hook means comprising a plate member folded over onto itself to form a track, and, a hook-shaped opening therein;
    cutting blade means mounted to said frame and movable, axially, within said track means; and
    actuating means mounted to said frame for moving said blade means in said track means axially through said hook means for cutting tissue or blood vessels engaged by said hook means.

* * * * *